US009375547B2

(12) United States Patent
Augustine et al.

(10) Patent No.: US 9,375,547 B2
(45) Date of Patent: Jun. 28, 2016

(54) PERSONAL AIR FILTRATION DEVICE

(71) Applicant: Augustine Biomedical & Design LLC, Eden Prairie, MN (US)

(72) Inventors: Scott D. Augustine, Deephaven, MN (US); Mark C. Albrecht, Minneapolis, MN (US); Randall C. Arnold, Minnetonka, MN (US); Ryan S. Augustine, Minneapolis, MN (US); Ryan Barrows, Eau Claire, WI (US); Andrew McGregor, Minneapolis, MN (US)

(73) Assignee: AUGUSTINE BIOMEDICAL AND DESIGN, LLC, Eden Prairie, MN (US)

( * ) Notice: Subject to any disclaimer, the term of this patent is extended or adjusted under 35 U.S.C. 154(b) by 0 days.

(21) Appl. No.: 14/807,034

(22) Filed: Jul. 23, 2015

(65) Prior Publication Data
US 2015/0328428 A1 Nov. 19, 2015

Related U.S. Application Data

(63) Continuation of application No. 13/158,879, filed on Jun. 13, 2011, now Pat. No. 9,144,697, which is a continuation of application No. 12/037,078, filed on Feb. 25, 2008, now abandoned.
(Continued)

(51) Int. Cl.
*A47C 21/04* (2006.01)
*A47G 9/10* (2006.01)
(Continued)

(52) U.S. Cl.
CPC .............. *A61M 16/105* (2013.01); *A47C 7/744* (2013.01); *A47C 21/044* (2013.01); *A47G 9/10* (2013.01); *A61M 15/0083* (2014.02);
(Continued)

(58) Field of Classification Search
CPC .... A47C 21/04; A47C 21/042; A47C 21/044; A47C 21/046; A47C 21/048; A47C 7/74; A47C 7/744; A47G 9/1036; A61G 2007/05784; A62B 23/00; B60N 2/56
See application file for complete search history.

(56) References Cited

U.S. PATENT DOCUMENTS

| 96,989 A | 11/1869 | Somes |
|---|---|---|
| 2,025,659 A | 12/1935 | Adolphe |

(Continued)

FOREIGN PATENT DOCUMENTS

| EP | 624340 A1 | 12/1998 |
|---|---|---|
| JP | 2005111048 A | 4/2005 |

(Continued)

OTHER PUBLICATIONS

Avidan et al., Convection Warmers, Not Just Hot Air, Anaesthesia, 1997, pp. 1073-10706, 52, Blackwell Science Ltd.
(Continued)

*Primary Examiner* — Valerie L Woodward
(74) *Attorney, Agent, or Firm* — Fredrikson & Byron, P.A.

(57) ABSTRACT

A personal air filtration device and methods of using the same for providing a zone of filtered air proximate a breathing zone of a user are described. A blower provides an air flow to a head support which delivers the air flow to a zone proximate the users head. The air flow passes through a filter. The filter can be a point of delivery filter disposed about an air permeable surface of the head support. The delivered air flow can provide a laminar air flow defining a zone of filtered air about the user's breathing zone.

29 Claims, 7 Drawing Sheets

Related U.S. Application Data

(60) Provisional application No. 60/891,708, filed on Feb. 26, 2007, provisional application No. 60/891,390, filed on Feb. 23, 2007, provisional application No. 60/891,395, filed on Feb. 23, 2007, provisional application No. 60/891,400, filed on Feb. 23, 2007.

(51) Int. Cl.

| | |
|---|---|
| *A47C 7/74* | (2006.01) |
| *A62B 23/00* | (2006.01) |
| *A61M 16/10* | (2006.01) |
| *A61M 16/00* | (2006.01) |
| *A61M 16/06* | (2006.01) |
| *A61M 16/08* | (2006.01) |
| *A61M 15/00* | (2006.01) |
| *A61M 15/08* | (2006.01) |
| *A61M 16/14* | (2006.01) |
| *A61M 16/16* | (2006.01) |

(52) U.S. Cl.
CPC .......... *A61M 16/0066* (2013.01); *A61M 16/06* (2013.01); *A61M 16/0627* (2014.02); *A61M 16/0875* (2013.01); *A61M 16/107* (2014.02); *A61M 16/108* (2014.02); *A62B 23/00* (2013.01); *A61M 15/08* (2013.01); *A61M 16/14* (2013.01); *A61M 16/16* (2013.01); *A61M 2205/42* (2013.01); *A61M 2205/75* (2013.01); *A61M 2209/088* (2013.01)

(56) References Cited

U.S. PATENT DOCUMENTS

| | | | | |
|---|---|---|---|---|
| 2,493,067 | A | * | 1/1950 | Goldsmith .......... A47C 21/044 219/217 |
| 3,266,064 | A | | 8/1966 | Figman |
| 3,653,083 | A | | 4/1972 | Lapidus |
| 3,724,172 | A | | 4/1973 | Wood |
| 3,820,536 | A | | 6/1974 | Anspach et al. |
| 3,941,697 | A | | 3/1976 | Johnson |
| 4,391,009 | A | | 7/1983 | Schild et al. |
| 4,398,535 | A | | 8/1983 | Guibert et al. |
| 4,818,122 | A | | 4/1989 | Arbuthnot |
| 4,977,634 | A | | 12/1990 | Koji |
| 5,160,517 | A | | 11/1992 | Hicks et al. |
| 5,247,714 | A | | 9/1993 | Lipps |
| 5,304,213 | A | | 4/1994 | Berke et al. |
| 5,305,483 | A | | 4/1994 | Watkins |
| 5,312,465 | A | | 5/1994 | Riutta et al. |
| 5,317,767 | A | | 6/1994 | Hargest et al. |
| 5,389,037 | A | | 2/1995 | Hale |
| 5,473,783 | A | * | 12/1995 | Allen .................... A47C 21/044 5/423 |
| 5,588,698 | A | | 12/1996 | Hsueh |
| 5,640,728 | A | * | 6/1997 | Graebe .................. A47C 7/744 5/423 |
| 5,733,320 | A | | 3/1998 | Augustine |
| 5,785,723 | A | | 7/1998 | Beran et al. |
| 5,876,428 | A | | 3/1999 | Van Duren et al. |
| 5,902,365 | A | | 5/1999 | Haggard et al. |
| 6,230,350 | B1 | | 5/2001 | Goldstein |
| 6,261,332 | B1 | | 7/2001 | Richard |
| 6,440,157 | B1 | | 8/2002 | Shigezawa et al. |
| 6,447,538 | B1 | | 9/2002 | Van Duren et al. |
| 6,546,576 | B1 | * | 4/2003 | Lin ....................... A47C 21/048 5/423 |
| 6,702,662 | B2 | | 3/2004 | Kristensson et al. |
| 6,988,293 | B2 | | 1/2006 | Ritter |
| 7,037,068 | B2 | | 5/2006 | Cobb et al. |
| 7,037,188 | B2 | | 5/2006 | Schmid et al. |
| 7,063,087 | B2 | | 6/2006 | Cerbini et al. |
| 7,118,608 | B2 | | 10/2006 | Lovell |
| 7,195,660 | B2 | | 3/2007 | Little et al. |
| 7,279,021 | B2 | | 10/2007 | Häberlein et al. |
| 7,370,380 | B2 | | 5/2008 | DeFranks et al. |
| 7,607,433 | B2 | | 10/2009 | Silva et al. |
| 9,144,697 | B2 | * | 9/2015 | Augustine .............. A62B 23/00 |
| 2003/0033790 | A1 | | 2/2003 | Hague |
| 2003/0036786 | A1 | | 2/2003 | Duren et al. |
| 2003/0084510 | A1 | | 5/2003 | Lin |
| 2003/0089233 | A1 | | 5/2003 | Borla |
| 2003/0150328 | A1 | | 8/2003 | Hansson et al. |
| 2004/0112381 | A1 | | 6/2004 | Ujhazy et al. |
| 2004/0244595 | A1 | | 12/2004 | Elliot |
| 2005/0229557 | A1 | | 10/2005 | Little et al. |
| 2005/0278863 | A1 | * | 12/2005 | Bahash ................ A01K 1/0353 5/726 |
| 2006/0271134 | A1 | | 11/2006 | Frey |
| 2007/0240719 | A1 | | 10/2007 | Duarte |
| 2008/0020695 | A1 | | 1/2008 | Chang |

FOREIGN PATENT DOCUMENTS

| | | |
|---|---|---|
| WO | 9711625 A1 | 4/1997 |
| WO | 2005027699 A1 | 3/2005 |

OTHER PUBLICATIONS

PCT Application No. PCT/US2008/054928, International Search Report and Written Opinion, dated Jul. 11, 2008, 10 pages.
PCT/US2009/036260, Invitation to Pay Additional Fees and Partial International Search Report, dated Jul. 10, 2009.
PCT Application No. PCTIUS2009I059721, International Search Report and Written Opinion, dated Nov. 17, 2009, 7 pages.

* cited by examiner

PERSONAL AIR FILTRATION DEVICE

PRIORITY CLAIM

The present application is a continuation of U.S. patent application Ser. No. 13/158,879, entitled PERSONAL AIR FILTRATION DEVICE filed on Jun. 13, 2011, which claims priority to U.S. patent application Ser. No. 12/037,078, entitled PERSONAL AIR FILTRATION DEVICE filed on Feb. 25, 2008, which claims priority to provisional application Ser. No. 60/891,395, entitled PERSONAL AIR FILTRATION DEVICE filed on Feb. 23, 2007; Ser. No. 60/891,390, entitled PERSONAL AIR FILTRATION DEVICE filed on Feb. 23, 2007; Ser. No. 60/891,400, entitled PERSONAL AIR FILTRATION DEVICE filed on Feb. 23, 2007; and Ser. No. 60/891,708, entitled PERSONAL AIR FILTRATION DEVICE filed on Feb. 26, 2007, all of which are incorporated by reference in their entireties herein.

TECHNICAL FIELD

The present invention is related to air filtration devices. In particular the invention relates to air filtration devices which direct filtered air to a sleeping or resting person.

BACKGROUND

It is estimated that 1 in 5 Americans suffer from allergic rhinitis/conjunctivitis (AR). AR is the result of an IgE mediated immune system response to inhaled aero-allergens, which typically include dust mite, fungi, animal dander, pollutants, molds, and pollens. For those individuals afflicted by AR, the short term effects extend beyond the physical symptoms found in the eyes and nose, often resulting in cognitive impairment, sleep disturbance, lowered work/school productivity, and reductions in quality of life. More alarmingly, if AR symptoms persist on a long term basis the disease can lead to the development of comorbities, including asthma, sinusitis, otiis media, nasal polyposis, lower respiratory tract infection, and dental malocclusion.

Typical treatment for AR consists of three steps. First, the trigger allergen(s) is identified and environmental control measures are employed to minimize allergen exposure. Second, if elimination steps are unsuccessful, medication is employed to manage and control symptoms. Third, for perennial allergen exposure, immunotherapy may be undertaken to obtain long term symptom control. Allergen avoidance is the preferred treatment, providing symptom resolution absent medication. But to date few allergen avoidance measures exist that reduce airborne allergen concentrations to a clinically relevant level.

Effective allergen avoidance focuses on two basic principles: identification of the offending allergen source, and removal/elimination of the offending source or reduction of the concentration of inhaled aero-allergens. Commonly practiced allergen avoidance measures that are clinically effective include pet removal from the home and geographic re-location. Other forms of allergen avoidance that are of questionable clinical effectiveness but are commonly practiced include whole room air filtration, dust mite casings, use of air conditioning, and carpet removal.

Of the listed allergen avoidance measures, air filtration systems, some of which remove particulates at 99.97% efficiency, show great promise for reducing inhaled aero-allergen concentrations to a clinically relevant level. However, the current practice of such technologies limit their effectiveness. For example, people often utilize room air cleaner units in an attempt to achieve a reduction in particle levels within a localized area. These types of units effectively remove a high percentage of harmful particles from the air that flows through the unit. However, individuals within the area of the unit may not experience all of the beneficial results of this particle removal because the air that is discharged from the unit is able to pick up additional harmful particles from the surrounding environment prior to reaching and being breathed in by the individuals. Furthermore, the effectiveness of air cleaners and purifiers is greatly affected by the size of the room, such that results worsen as the room size increases. Other room factors such as air-tightness, the presence of air currents and traffic which can kick up particles, also affect the performance of air cleaners and purifiers. In the case of dust mites residing in bedding, a room air filter can not adequately reduce the allergenic exposure between the bedding and the person sleeping in the bed. Given these factors, it is difficult for an air cleaner or purifier to significantly reduce the levels of allergens and pollutants being breathed by an individual.

Prior art air cleaners have attempted to reduce these problems by directing air directly into the face of a sleeping person. Such devices must blow a considerable wind on to the sleeping person's head in order to prevent ambient particles from circulating near the person while sleeping. Such high wind levels may be annoying to a person who is trying to sleep. Furthermore, many of these devices are cumbersome, expensive and unsightly.

SUMMARY

In one aspect, the invention provides a device for providing a zone of filtered air proximate a breathing zone of a user. In certain embodiments, a blower is configured to provide an airflow to a head support. At least a portion of a surface of the head support is air permeable in such embodiments, and a filter is disposed in flow communication with air flow provided by the blower. Positioning the head support underneath the user's head allows the air flow to be delivered through the air permeable portion to create a zone of filtered air proximate the breathing zone of the user. In some embodiments, the filter can be disposed downstream from the blower, for example as a point of delivery filter.

In another aspect, a method of creating a zone of filtered air proximate a breathing zone of a user is provided. In certain embodiments, a blower, a plenum in flow communication with the blower, having an air permeable surface, and a filter disposed in flow communication with the blower are provided. The plenum is positioned in close proximity to the breathing zone of the user. The blower is actuated, thereby providing airflow to the plenum. The airflow is directed through the filter. The airflow is directed to the plenum, thereby causing the plenum to inflate and direct the air flow through the air permeable portion of the plenum.

In yet another aspect, a method of providing a user with filtered air is provided. In this aspect, an air delivery surface is provided in support of the head of the user. A laminar filtered air flow is then provided through the air delivery surface that surrounds a breathing zone of the user. Such a laminar air flow can prevent airborne environmental contaminants from entering the user's breathing zone.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Those skilled in the art will recognize that many of the examples provided have suitable alternatives that can be utilized.

Embodiments of the invention comprise a device and method for providing a flow of filtered air to a breathing zone of a person without blowing a high volume of air toward the person's face. The head of the user rests on top of a head support, through which the air is delivered. As a result, filtered air can be delivered directly to a space around the user's head or breathing zone. In this way, filtered air can be delivered without the need to filter the air of the entire room, making filtration more efficient and effective. By decreasing the amount of time and distance between the release of air from the device and inhalation by the user, the amount of recontamination of the filtered air is decreased. In addition, the continuous flow of filtered air into the breathing zone prevents unfiltered, contaminated air from the environment from entering the breathing zone due to inhalation by the user or current flow within the environment. Moreover, the zone of filtered air can be maintained at a low flow rate, reducing unwanted noise and the feeling of wind blowing on the sleeping person's face.

Figure 1:
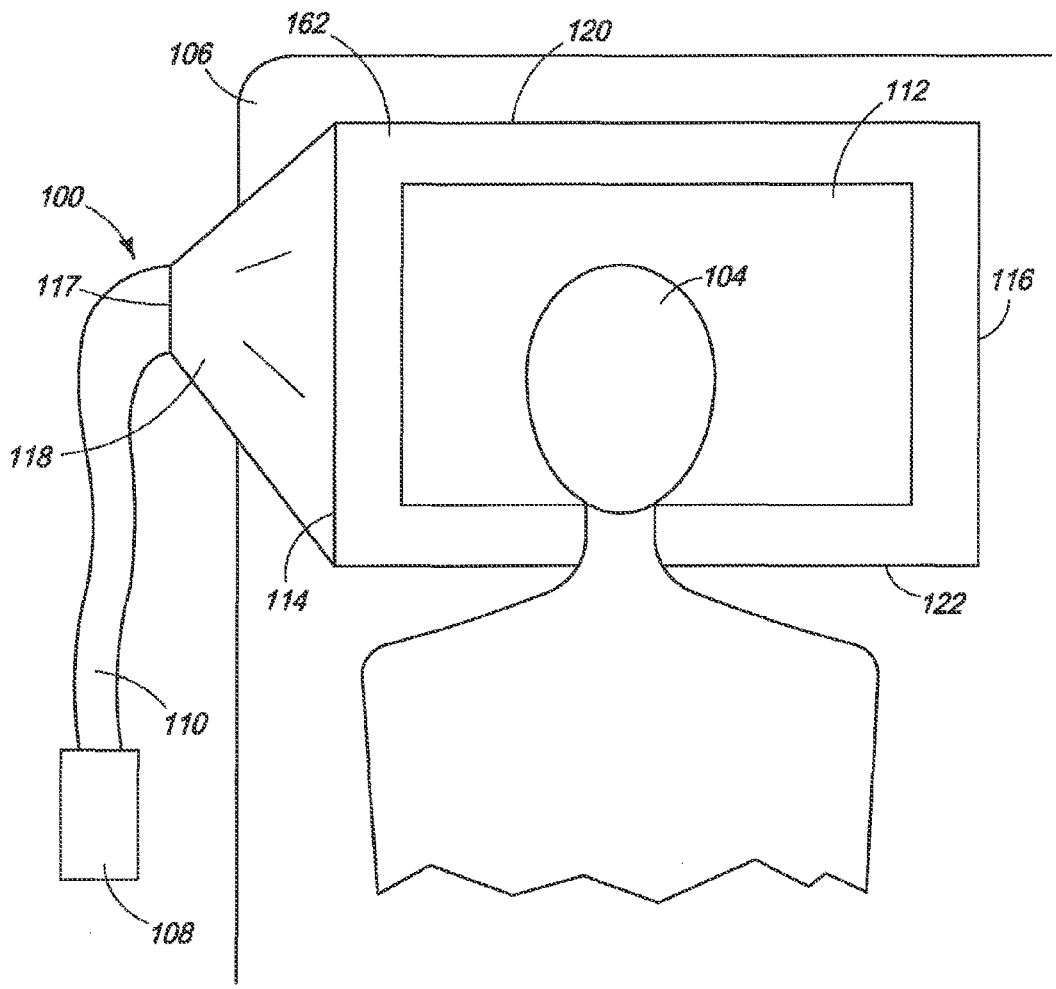
FIG. 1 is a top plan view of a personal air filtration device in use according to embodiments of the invention.

FIG. 1 shows an embodiment of a personal air filtration device 100 in use. In this embodiment, a head support 102 is positioned beneath a user 104 lying on a bed 106. The head support 102 is coupled in flow communication to a blower 108 by a hose 110. Blower 108 can provide air flow through the hose 110 and into a plenum within the head support 102. As air flow accumulates within the head support 102 the plenum inflates causing air to exit the head support 102 through an air permeable portion 112. As the air leaves the head support 102 it is filtered by a point of delivery filter positioned within the plenum substantially coextensive with the air permeable portion 112. As described above, such an arrangement can provide an efficient, effective delivery of filtered air to the breathing zone of the user 104.

Figure 7:
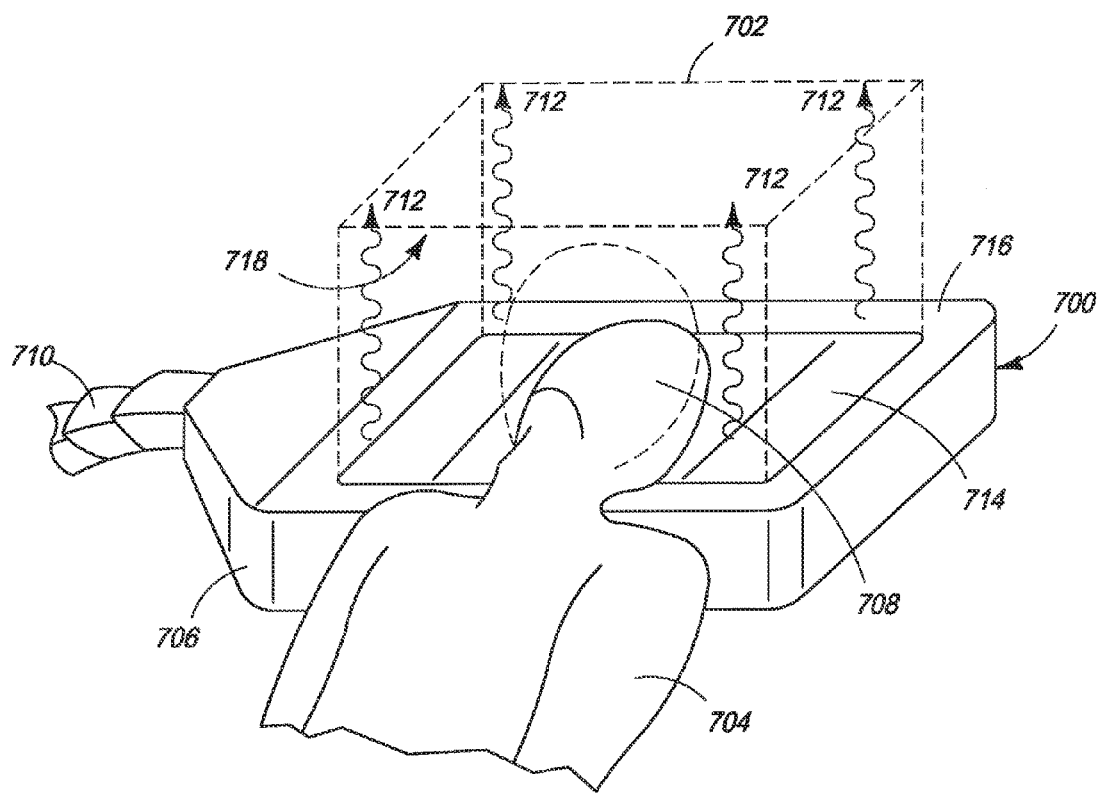
FIG. 7 is a perspective view of a personal air filtration device in use according to some embodiments.

FIG. 7 illustrates how an embodiment of a personal air filtration device 700 can be used to provide a volume or bubble of filtered air 702 to a user 704. The user 704 is shown lying upon head support 706 with dotted lines depicting the breathing zone 708 of the user 704. The breathing zone 708 is a volume of air proximate the user 704 and available for inspiration. Generally the breathing zone is located proximate the user's head, and more specifically proximate the mouth and of nose of the user. The size of the breathing zone 708 can vary depending upon the user's lung capacity, depth of breathing, breathing rate, and other factors. In many adults, the breathing zone 708 can represent a volume of approximately 1-10 liters of air, however smaller or larger volumes are contemplated. When breathing, a user 704 draws air from the breathing zone 708 and into his or her lungs. Therefore, by ensuring that the breathing zone 708 includes only filtered air, one can be sure that the user inhales only filtered air.

Embodiments of the invention provide filtered air to the breathing zone 708 by creating a bubble of filtered air 702 to encapsulate the user's breathing zone 708. In operation, a blower (not shown) can provide a flow of air to the head support 706 through a hose 710. The head support 706 disperses the air and provides a filtered air flow 712 through an air permeable portion 714 of its upper surface 716. This filtered air flow 712 provides a supply of filtered air to the bubble 702 and prevents unfiltered environmental air from reaching the breathing zone 708. As the user 704 breathes, air is inhaled, and thereby displaced from the breathing zone 708. This displaced breathing zone air is then replaced with filtered air from the bubble 702, to the exclusion of unfiltered environmental air.

Moreover, the filtered air flow 712 can prevent currents of unfiltered environmental air 718 from penetrating the breathing zone 708. Disturbances in the environment (such as, for example, moving people, animals, or fans) or inhalation from a user 704 can cause unfiltered environmental air (i.e. air outside of the bubble 702) to move and form currents. Such currents 718 could penetrate the breathing zone 708 and be inhaled, mitigating the benefits of providing filtered air to the user. However, the continuous, laminar filtered air flow 712 provided by embodiments of the invention can act like a curtain, sweeping these currents 718 away from and out of the breathing zone 708 (as illustrated by the curved portion of arrows 718 in FIG. 7). As such, the bubble 702, can provide a reservoir of filtered air to user for inspiration. In some embodiments, the bubble 702 can be defined as a volume of air having a particle count less than 100,000 particles 0.3 micrometers (μm) or greater in diameter per cubic foot. Or the bubble 702 may be defined terms relative to the ambient particulate concentration, e.g. a volume having particle count at less than 50% of that of the surrounding environment. Further, in many embodiments, the bubble 702 created by the device is at least as large as the breathing zone 708 of the user and positioned such that the breathing zone 708 is positioned entirely within the bubble 702. Preferably, the bubble 702 is at least twice the size of the breathing zone 708. And while the embodiments discussed above have defined a bubble 702 as being positioned about or around a user's head, one should recognize that other arrangements, such as creating a bubble 702 off to one side of a user's head, are contemplated.

Figure 2:
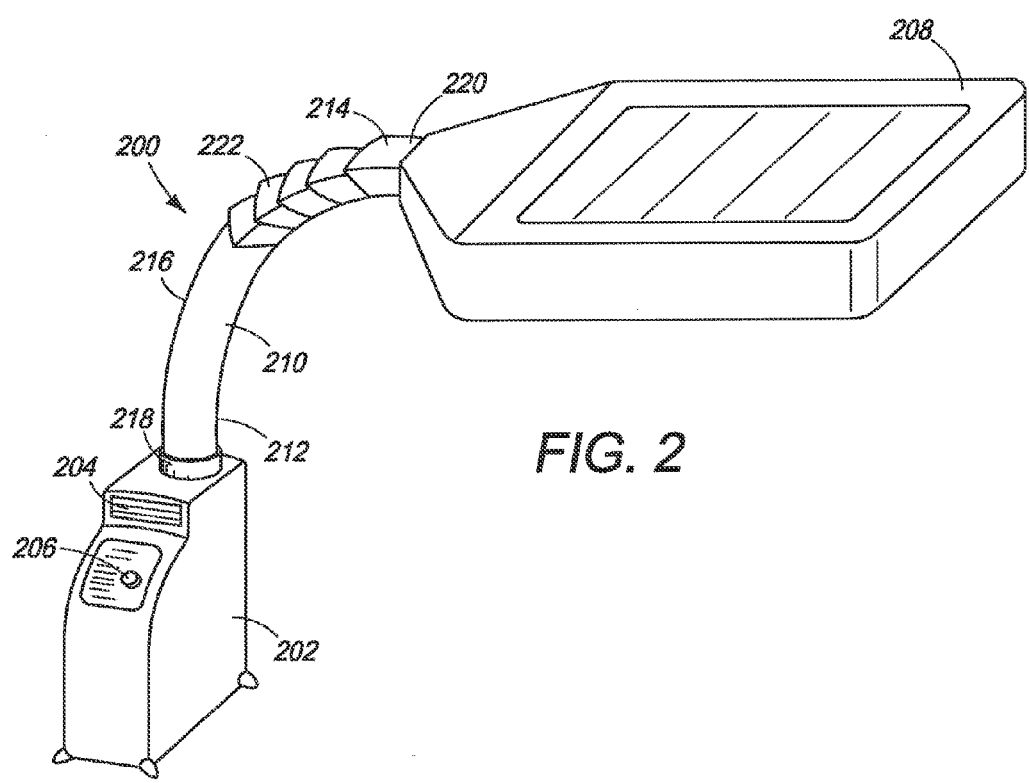
FIG. 2 is a perspective view of a personal air filtration device according to embodiments of the invention.

In the embodiment of FIG. 2 additional features of an air filtration device 200 are apparent. The blower 202 includes an air intake port 204 for drawing air into the system from the surrounding environment. The blower 202 may be placed in proximity to a bed, such as on a night stand, next to the bed, or concealed under the bed, adjacent to or near the head of the sleeping or resting user. It is preferably small to allow for easy transportation and concealment. Also, due to the proximity of the blower 202 to the bed during use, blower 202 is relatively quiet. For example, in one embodiment, a blower produces a maximum noise level of approximately 60 decibels. The blower should be adapted to provide air at a flow rate capable of sustaining a zone of filtered air of at least one liter about the breathing zone of a user. In some embodiments, such a flow rate can range from 1 cubic foot per minute to 100 cubic feet per minute.

A blower 202 can include one or more control knobs 206, buttons or other interface means for controlling blower speed or other optional features. For example, the blower 202 may optionally include a component which produces white noise to obscure any noise produced by the blower. Other optional features which may be included in the blower include a temperature control to heat or cool the air, an air humidifier, a medication dispenser, and/or an aroma dispenser. These optional features may be controlled manually or automatically, such as by a timing mechanism. For example, a stimulating aroma such as mint or citrus may be emitted in the morning to function as an alternative to, or in addition to, an audible alarm. A soothing aroma such as lavender may be emitted while the user is going to sleep and could automatically stop after a preset amount of time. Moreover, in some embodiments, the blower 202 may include one or more filtration mechanisms (e.g. an ultraviolet radiation filter, a carbon-based filter, or a HEPA or other mechanical filter). An air intake filtration mechanism may be positioned proximate the air intake port 204 to filter air as it is drawn into the blower 202. Alternatively, a filtration mechanism may be placed near the air outlet to filter the air as it leaves the blower 202. Embodiments including a blower 202 having a filtration mechanism may or may not include an additional filter positioned downstream of the blower, such as those discussed below.

The blower 202 can be coupled with the head support 208 by a hose 210. The hose can have a proximal section 212 which is attached to the blower 202, a distal section 214 which is attached to the head support 208, and a middle section 216 connecting the proximal and distal sections 212, 214. In some embodiments, the hose 210 can include a detachable attachment mechanism 218 at one or both ends for detachably coupling the hose 210 to the blower 202, the head support 208, or both. Examples of detachable attachment mechanisms 218 can include threaded cuffs, tapered joints, grooved joints, or other mechanisms known in the art. The hose 210 may be comprised of a rigid or semi-rigid material to prevent collapse. Alternatively, the hose 210 may be comprised of a collapsible material, such as fabric or polymeric foam. Such a collapsible hose would inflate when air pressure is applied and would not feel like a hard object if the user places an arm or hand on the hose during the night. In some embodiments, the hose 210 is composed of both a rigid or semi-rigid material and a collapsible material. For example, in one embodiment, the hose 210 is rigid in the proximal and middle sections 212, 216 and is collapsible in the distal section 214. Such a hose 210 may include semi-rigid support members, such as a coil, near the air inlet 220. The hose 210 may optionally include a formed elbow to transition the airflow from a substantially vertical direction to a substantially horizontal direction. Such an elbow may also function to maintain the position of the hose 210 on the bed.

Figure 3A:
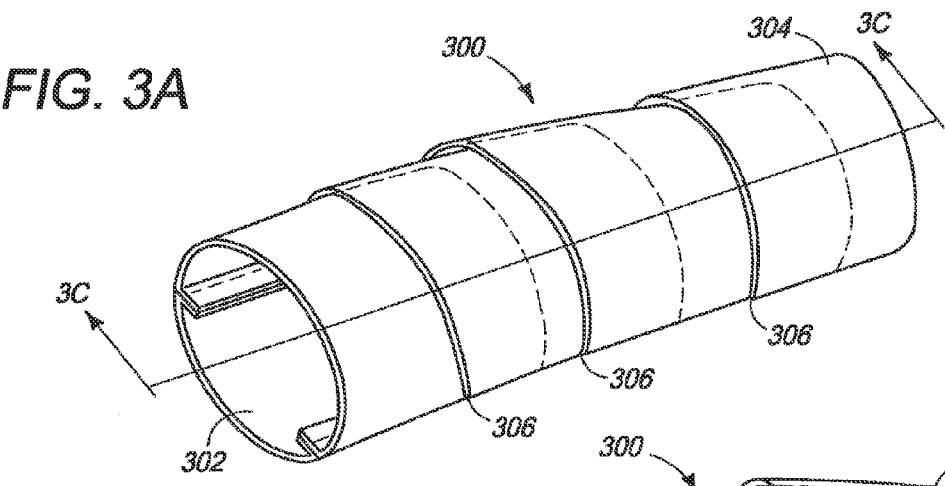
FIG. 3A is a perspective view of a portion of hose according to embodiments of the invention.
Figure 3B:
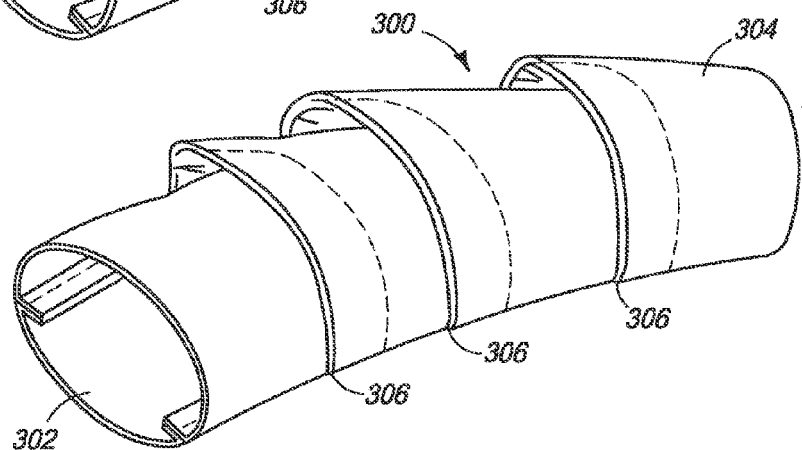
FIG. 3B is a perspective view of a portion of hose, one side having been extended according to embodiments of the invention.
Figure 3C:
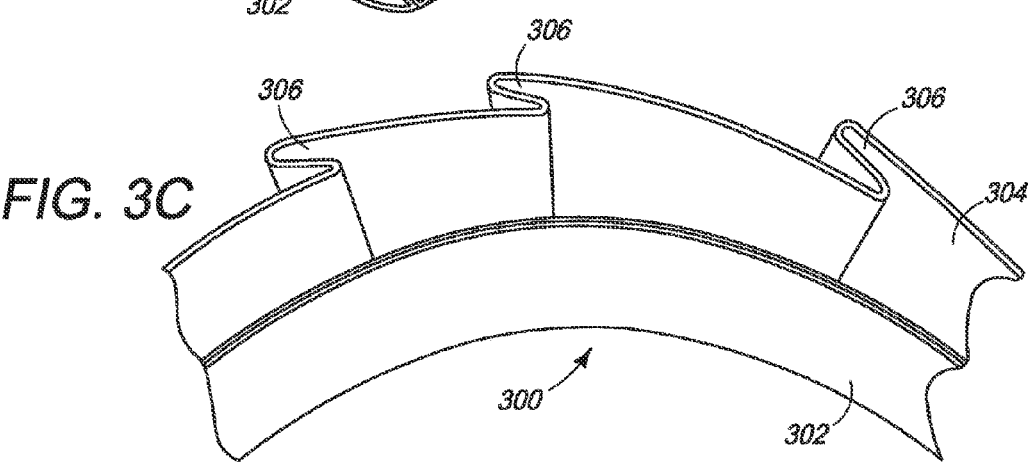
FIG. 3C is a cross sectional view of a portion of a hose according to embodiments of the invention.

In some embodiments, the hose 210 or a portion thereof is comprised of a flexible material such as an air impermeable fabric and includes pleats 222 to prevent the hose 210 from collapsing when bent. An example of such an embodiment is shown in FIGS. 3A-3C. The hose 300 includes a first surface 302 and a second surface 304. The width of the first surface 302 is less than that of the second surface 304, such that the second surface 304 forms a greater portion of the circumference of the hose 300 than the first surface 302. The difference in widths of the first and second surfaces 302, 304 assists the second surface 304 in forming an arch relative the first surface 302, helping the hose to stay open and assisting with air flow.

The hose 300 may include pleats 306 over a portion or all of the hose 300. In the embodiment shown in FIGS. 3A-3C the second surface 304 of the hose 300 is pleated relative to the first surface 302. The pleats 306 allow the hose 300 to bend without narrowing the space inside the hose 300, preventing the restriction of air flow when the hose 300 is bent. As shown in FIG. 3A, when the hose 300 is straight, the pleats 306 in the second surface 304 of the hose cover 21 fold in upon themselves, shortening the length of the second surface 304. When the hose bends toward the first surface 302 (see e.g. FIG. 3B), the pleats 306 in the second surface 304 open up, allowing the second surface 304 to become longer such that the space within the hose 300 is not compressed. In some embodiments, the first surface 302 of the hose 300 lies adjacent to the bed and the pleats 306 extend over the elbow portion of the hose 300, allowing the hose 300 to bend as it extends around the edge of the bed without compressing or kinking.

Figure 4:
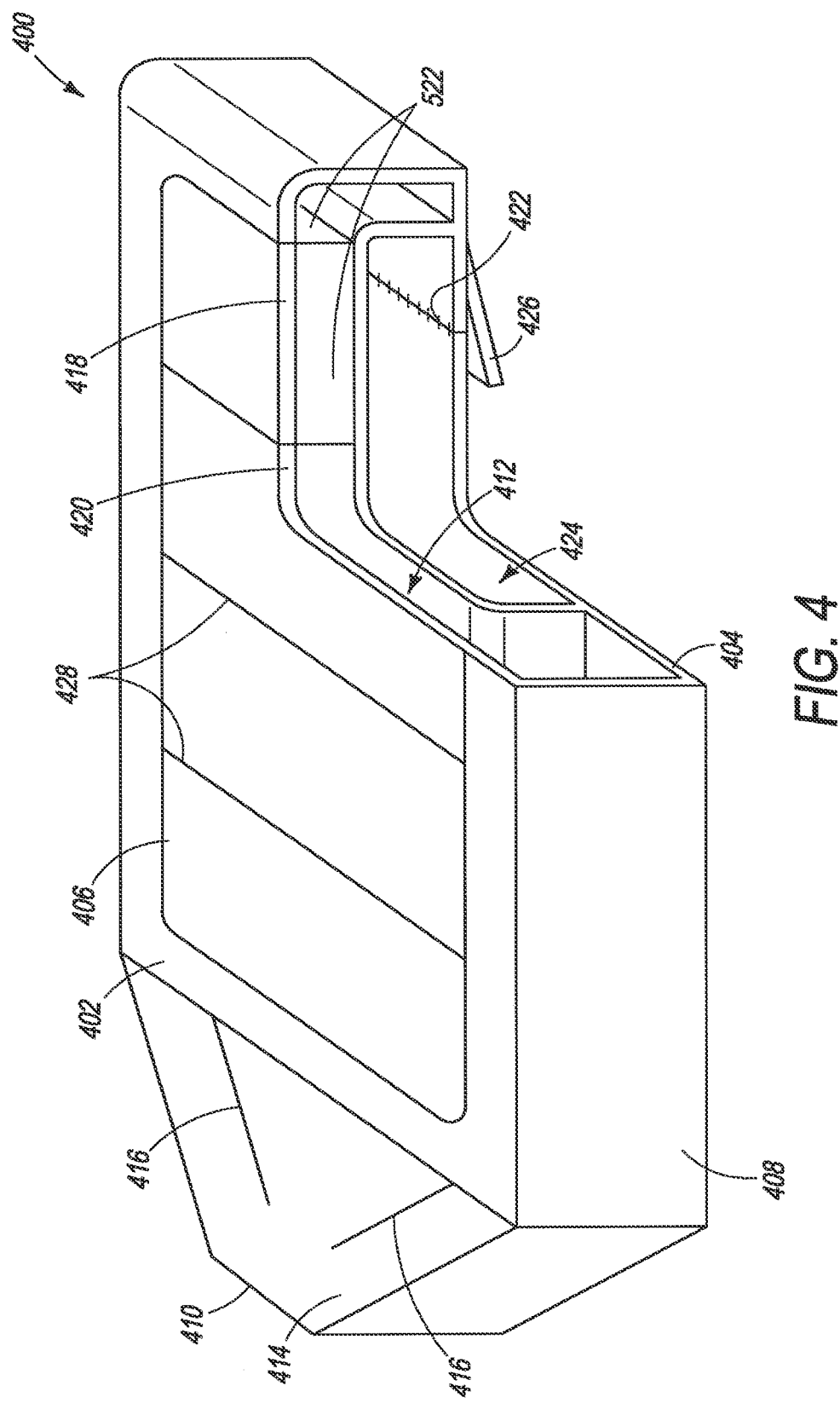
FIG. 4 is a partial cut away perspective view of a head support according to embodiments of the invention.

Referring back to FIG. 2, the distal section 214 of the hose 210 can be seen to connect to the head support 208 at an air inlet 220. The hose 210 may be permanently attached to the air inlet 220 or may be detachable from the head support 208 as described above. FIG. 4 shows a perspective view of an embodiment a head support 400 having a portion cut away to reveal internal features. The head support 400 can include an upper surface 402 to be positioned adjacent to the user's head, and a lower surface 404 to be positioned adjacent to a the bed. A portion 406 or all of the upper surface 402 is air permeable while the lower surface 404 is generally air impermeable. The upper and lower surfaces 402, 404 should be constructed of a soft, pliable material so that a user can comfortably lay his or her head atop the device. In some embodiments, the upper and lower surfaces can be coupled together along their respective edges at a seam or other air tight joint. Other embodiments, such as that of FIG. 4 can include a side panel 408 for joining the upper and lower surfaces 402, 404. A side panel 408 can be constructed of a generally air impermeable material, such as the material used to construct the lower surface 404. In a preferred embodiment, the air impermeable surfaces are constructed of micro fiber Polyester or coated Nylon Supplex coated both of which are available from Dupont. The upper and lower surfaces 402, 404 can be connected to the side panel 408 by any means suitable for creating a generally air tight connection, such as sewing, adhesive, or thermal bonding.

Head support 400 also includes an air inlet 410. The air inlet 410 can be a hole through a side panel 408 or, in embodiments not including a side panel, a gap in the connection between the upper and lower surfaces. The air inlet 410 provides a flow connection between the head support 400 and the blower. In some embodiments, the air inlet 410 can include a detachable joint mechanism for detachably coupling a hose to the head support 400.

In some embodiments, the surfaces of the head support 400 bound a plenum 412 to be filled with air supplied by the blower. The plenum 412 provides a chamber within the head support 400 where air can gather and disperse prior to the air escaping through the permeable portion 406 of the upper surface 402 and into the space surrounding the head of the user. In this way the plenum 412 allows air to be delivered generally uniformly across the entire surface area of the air permeable portion of the upper surface.

To further assist the uniform distribution of air flow from the plenum 412, some embodiments include an inlet manifold 414. An inlet manifold 414 can be a fan-shaped portion of the head support 400 or a separate component disposed between the plenum 412 and the air inlet 410. In some embodiments, the inlet manifold 414 can include internal air guides 416 to assist in evenly distributing air flow from the air inlet 410 to the plenum 412. Internal air guides 416 can be panels disposed within the manifold 414 so as to cause air to diverge upon entering head support 400 through the air inlet 410. A secondary purpose of the internal air guides 416 is to maintain the manifold in a flattened shape and prevent the surfaces from bulging upward under pressure. An inlet manifold 414 can be constructed of an air impermeable material such as the material used to construct the lower surface 404 of the head support 400.

A personal air filtration device according to the invention includes a filter 418 to filter the air flow that is to be delivered at the air permeable portion 406 of the head support 400. In some preferred embodiments, the filter 418 is disposed downstream from the blower. The filter 418 may be comprised of a material which provides HEPA (high efficiency particulate air) levels of filtration, such as Technostat® (available from Hollingsworth & Vose Company of East Walpole, Mass.). In some embodiments, a layer of activated charcoal may be added, possibly adjacent to the filter, for providing odor reduction.

Many arrangements can be used to position a filter downstream from a blower, for example, a filter can be placed at the air inlet 410 of head support 400, within an air inlet manifold 414, or within a hose. Each of these arrangements and others are contemplated and should be considered within the scope of the present invention. In some preferred embodiments, the filter can be a point of delivery filter. Such a filter can be seen in the embodiment of FIG. 4. In this arrangement, a filter 418 is disposed about and coextensive with the air permeable portion 406 of the head support 400, i.e. at the point of delivery of the air flow to the breathing zone. A point of delivery filter may be preferred for at least several reasons. First, because the filter 418 is generally coextensive with the air permeable portion 406 of the head support 400, the air can be filtered through a relatively large surface area. As a result, the pressure drop induced as the air traverses the filter 418 is much less than that caused by traversing a smaller surface area of the same filter material. Because of the reduction in pressure and air flow, the blower can perform more quietly while still producing an adequate volume of filtered air. Second, by locating the filter 418 on the upper surface 402 of the head support 400, a point of delivery filter causes the air flow to be filtered immediately prior to it entering the breathing zone. Therefore, the air is less likely to be contaminated post-filtration by environmental factors that may be present. By contrast, an air flow filtered in the blower, for example, would be subject to environmental contaminants present in the hose, inlet manifold, and plenum prior to entering the breathing zone.

As shown, the edges of the point of delivery filter 418 form a permanent and air tight connection with the air impermeable portion of the upper surface 402 of the head support 400. In such embodiments, the entire head support may be periodically washed or disposed of and replaced as needed. Alternatively, the filter may be removably attached to the air impermeable portion by filter attachment elements such as adhesive, hook and loop fasteners (e.g. Velcro), zippers, and/or other forms of attachment. A removable filter can be removed for cleaning of the filter or head support, or may be replaced periodically without requiring replacement of the entire head support.

In some embodiments, the filter material may be somewhat friable such that small fibers may break off of the filter surface, such as when contacted by a user's face during sleep. In addition, the user may find the feeling of the filter against his or her face to be unfamiliar. To prevent these problems, the upper surface 402 may include a filter cover 420. The filter cover 420 can be made of a material which is air permeable to allow filtered air to pass through from the filter 418 to the user's breathing zone. As an example, in one embodiment, a filter cover made of 220 thread-count Teflon coated cotton or satin can be used. Such a filter cover 420 may feel more comfortable or more familiar to the user. It may also act as a barrier between the filter and the user's face so that fragments of the filter do not come into contact with the user. Further, in some embodiments, a filter cover may include a hydrophobic composition or treatment. Such a composition can be applied to or included in the filter cover to provide stain- or water-resistant properties.

In some embodiments, filter cover 420 can attach to the head support 400 at the edges of the filter 418 or it may be larger than the filter 418 and attach beyond of the edges of the filter 418. Only a portion of an edge of the filter cover 420 may attach to the head support 400, or the entirety of all edges of the filter cover 420 may attach to the head support 400. When the entire edge of the filter cover is attached to the head support 400, it can enclose the filter 418 such that any fibers that detach from the filter 418 are encased within the space between the filter 418 and the filter cover 420, so that they do not come into contact with the user. Alternatively, a filter cover may be removably attached to the head support such as by hook and loop attachment or zippers. Removable attachment along a portion or all of the edges of the filter cover may be desirable in embodiments in which the filter is removable for washing or replacement, to allow access to the filter. In alternate embodiments, the cover layer may be attached to the filter, which, in turn, attaches to the head support.

As an alternative or in addition to a cover layer, embodiments may include a pillow case for surrounding the head support 400 and making it more comfortable for a user. A pillow case can be similar to a standard pillow case but should be sized to fit around the inflated head support 400. When installed, the pillow case lies between the upper surface 402 and the user's head and between the lower surface 404 of the head support 400 and the bed. A suitable pillow case should be made of an air permeable material so as to allow the filtered air from the personal filtration device to pass through to the user's breathing zone.

Referring to FIG. 1, the edges of the head support 102 include a proximal edge 114 and a distal edge 116 opposite the proximal edge 114. The proximal edge 114 is the edge closest to the hose 110. In some embodiments, an air inlet 117 and/or inlet manifold 118 can be disposed between the proximal edge 114 and the hose 110. Head support 102 also has a first edge 120 which is the edge closest to the head of the bed 106 and a second edge 122 which is the edge closest to the foot of the bed 106. Embodiments of the invention may be used with the hose 110 on either side of the bed 106 by rotating the head support 102 such that the first edge 120 becomes the second edge 122 and the second edge 122 becomes the first edge 120. The first and second edges 120, 122 are thus interchangeable depending upon orientation during use. Moreover, in some embodiments, the air inlet 117 may be disposed within the first edge 120. Such an arrangement in combination with a flexible or adjustable hose could be used on either side of the bed by pivoting the hose to the desired direction as it runs off the head of the bed. While embodiments have thus far depicted the head support as having a generally rectangular shape, it should be appreciated that any shape may be used. For example, the head support may be square, round, oblong, or a combination of shapes. Embodiments having a different shape than that of FIG. 1, can likewise be positioned on either side of a bed by rotating the head support such that the attached hose is directed generally away from the user.

Figure 5:
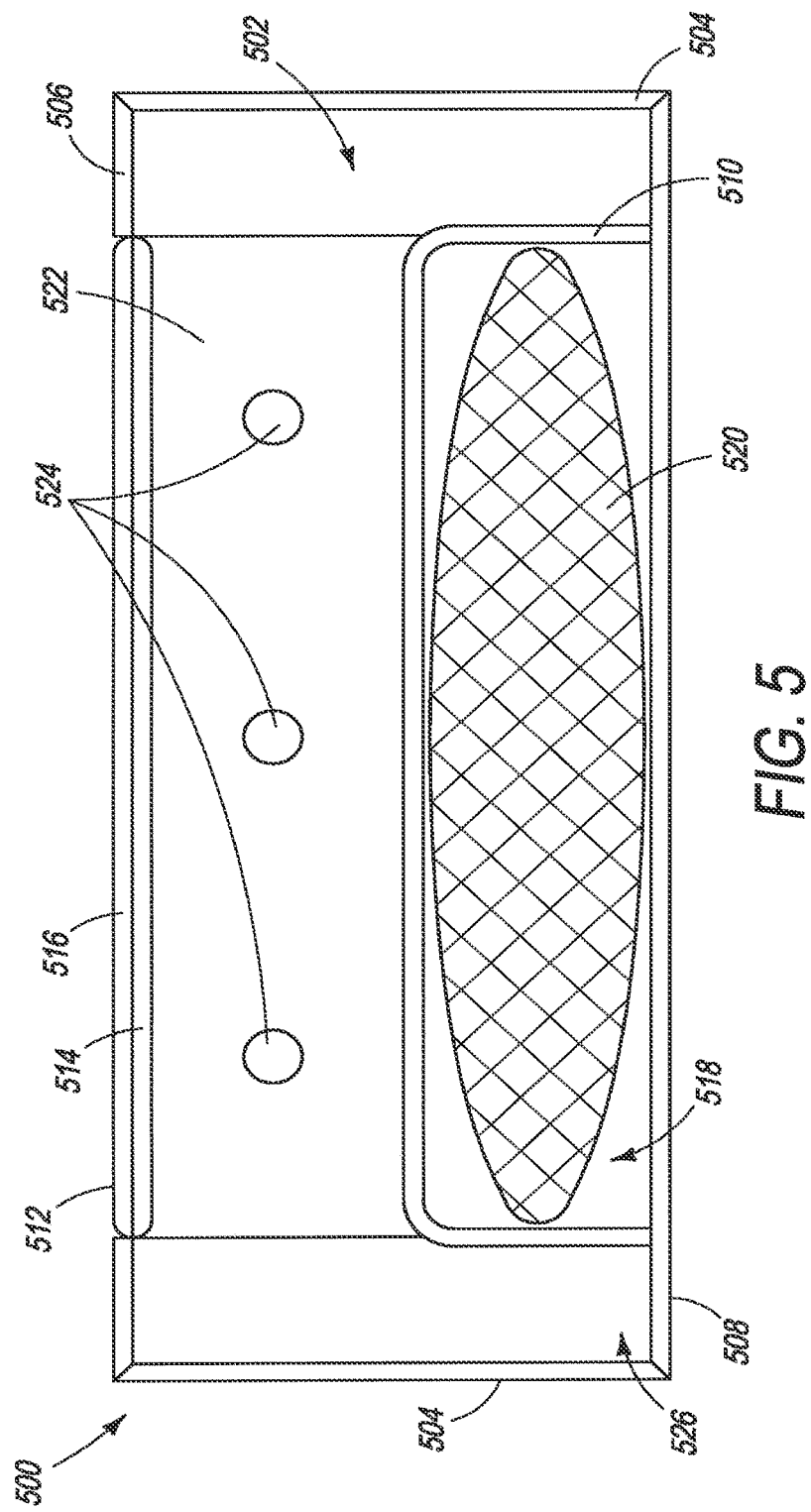
FIG. 5 is a cross-sectional view of a head support according to embodiments of the invention.

FIG. 5 is a cross-sectional view of a head support 500 according to some embodiments. From this view several internal features of a head support 500 are apparent. In this embodiment, the interior of the head support 500 includes a plenum 502 defined by side panels 504, top surface 506, bottom surface 508, and a pillow chamber wall 510. In operation, air flow accumulates within the plenum 502 and is passed through the air permeable portion 512 of the top surface 506. The air permeable portion 512 can include both a point of delivery filter 514 and a filter cover 516. A pillow chamber 518 including a pillow 520 is also disposed within the interior of the head support 500. In this embodiment, the pillow chamber is defined by pillow chamber wall 510 and the bottom surface 508 of the head support 500. The pillow chamber wall 510 may be constructed of the same air impermeable material as the bottom surface 508. The pillow chamber 518 can be sized so as to accommodate insertion of a standard or otherwise sized pillow. In some embodiments, a pillow can be sewn or sealed into a pillow chamber. Alternatively, embodiments such as that of FIG. 4 can include a zipper 422 or other access means for allowing a pillow to be inserted or removed from the pillow chamber 424. In such embodiments, an air impermeable flap 426 may be secured externally to cover the zipper 422 to prevent air from leaking through. Some embodiments do not include a pillow chamber, but include some other pillow connection means such as, for example, connectable straps running under the head support. Embodiments which include a pillow chamber having an access means or other pillow connection means can allow the user to select a preferred pillow to be used with the personal air filtration device.

In some embodiments, the plenum 502 can include support structures to facilitate proper air flow within and out of the head support 500. For example, the embodiments of FIGS. 4 and 5 include baffles 522 spanning the plenum 502 between the pillow chamber wall 510 and the top surface 506 of the head support 500. A baffle 522 can be used to restrict the expansion of the top surface 506 as the plenum 502 fills with air. Such restriction can be necessary to prevent doming of the air permeable portion 512 which can distort the direction in which air is released from the plenum 502 resulting in less effective delivery of air to the breathing zone. In some embodiments, baffles 522 can include internal air passages 524 to facilitate air flow throughout the plenum 502. Baffles 522 should be constructed of a soft, pliable material so as not to cause discomfort to a user resting upon the head support. For example, the baffles 522 could be constructed of the same material as the bottom surface 508 of the head support 500. Baffles 522 can be attached to the head support 500 by any suitable means, such as for example sewing, adhesive, or thermal bonding. Some baffle attachment means, such as stitching, may penetrate the surface to which the baffle is attached, resulting in air leakage points in the plenum 502. To prevent unfiltered air from escaping through these leakage points, some embodiments include an air impermeable seal along the baffle joint (e.g. over stitch 428 in FIG. 4).

The cross-section view of FIG. 5 further reveals that in some preferred embodiments, the pillow chamber 518 can be sized so that it is smaller than the head support 500. By this arrangement, a perimeter channel 526 can be defined by the side panel 504, the bottom surface 508, and the pillow chamber wall 510. A perimeter channel 526 can be advantageous in providing an even distribution of air throughout the plenum 502 when a user is resting upon the head support 500. With reference to FIG. 1, a user's head 104 resting on the head support 102 can cause an obstruction and block the flow of air from the proximal edge 114 to the distal edge 116 of a plenum within the head support 102. When the user 104 is lying on his or her side and facing the proximal edge 114, this would not present a problem because the user 104 would be facing the air inlet 117 and the air around the user's face would be filtered. However with the user's head on the head support 102, the flow of air to the distal edge 116 of the plenum would be at least partially obstructed. Therefore, the effectiveness of the personal air filtration device would be decreased when the user 104 is facing the distal edge 116.

The perimeter channel of FIG. 5 can prevent complete collapse of the plenum 502 and therefore provide for air flow to the partially obstructed distal portion of the plenum. Namely, when a user's head is placed on the head support the pillow 520 creates a height that lifts the user's head and neck above perimeter channel 526. In this manner, the perimeter channel 526 remains at least partially unobstructed, allowing air to flow to the region of the plenum 502 opposite the air inlet.

Further, some embodiments may include rigid or semi-rigid support structures within the plenum to maintain air flow across the plenum. Rigid or semi-rigid support structures can provide sufficient open space to allow air to flow through or around the structures. Such structures should be strong enough to prevent at least a portion of the plenum from completely collapsing against the pillow under the weight of a user's head while remaining flexible or soft enough so as not to disturb the user.

As discussed above, the head support may be adapted to be used with a pillow. Some embodiments may be adapted to contain a pillow (e.g. that of FIG. 4) while other embodiments can be adapted to lie on top of a pillow. In such embodiments, the head support may maintain this position in a variety of ways. For example, the head support may be attached to the pillow by including pillow attachment elements on the lower surface of the head support. Pillow attachment elements may be releasable, such as hook and loop fasteners, releasable adhesive, zippers, snaps or buttons. Other forms of pillow attachment elements which may be used include pouches and ties. Releasable forms of pillow attachment elements may allow the user the flexibility of using the personal air filtration device while continuing to sleep on a preferred pillow. In some embodiments, a pillow case may be used to hold the head support in position on top of a pillow. For example, the head support and a pillow could be placed together inside a single pillow case large enough to accommodate the pillow and the inflated head support. The pillow case may be used instead of, or in addition to, pillow attachment elements. When a pillow case is used, it should be comprised of an air permeable material in at least the portion overlying the air permeable portion to allow the release of the filtered air around the user's head.

Figure 6:
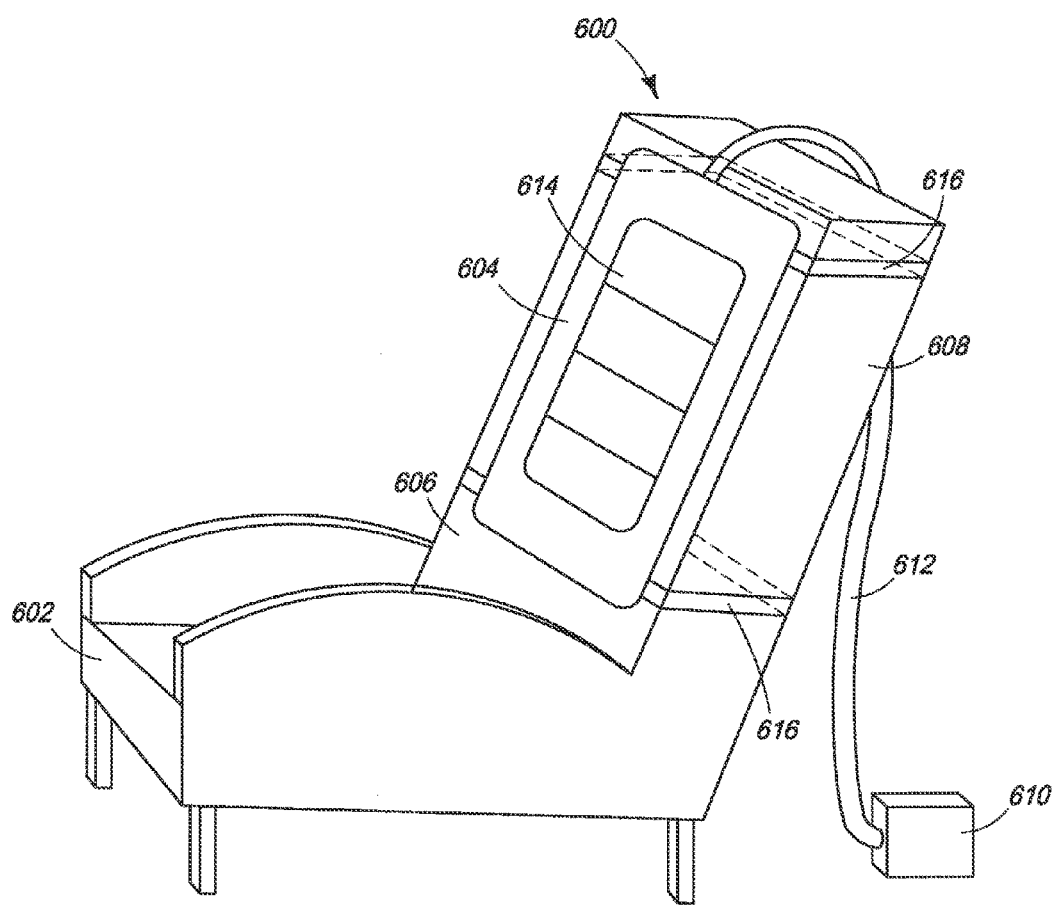
FIG. 6 is a perspective view of a personal air filtration device in use with a chair according to embodiments of the invention.

While the above embodiments have all described the personal air filtration device wherein the head support is used to support a user's head while the user lies on a bed, it should be understood that embodiments of the device can be used in other arrangements. For example, FIG. 6 shows a personal air filtration device 600 configured for use with a chair 602. Here, the head support 604 is positioned on the front surface 606 of the chair back 608. The lower surface of the head support 604 is positioned against the chair back 606 while the upper surface faces outward, toward the user's back.

When the personal air filtration device 600 of FIG. 6 is located on the front surface 606 of the chair back 608 as shown, the user rests the back of his or her head and/or back against the head support 604. Air is delivered from the blower 610, through the hose 612 and to the head support 604. The air inflates a plenum within the head support 604 and exits through the air permeable portion 614. The head support 604 can be arranged so that as air exits the air permeable portion 614, it is directed generally about the user's head. As a result, filtered air can be provided about the head and/or back of the user resulting in the same benefits as previously described with regard to other head support positioning.

Some embodiments can include attachment means for allowing for attachment of the head support 604 in various arrangements such as that of FIG. 6. For example, in the depicted embodiment, head support 604 includes one or more straps 616 to maintain its position on the chair back 608. Straps 616 can attach to any portion of the head support and can connect around a surface such as the chair back 608 to secure the head support 604 in place. The straps 616 may extend from one side of the head support to the opposite side of the head support as seen in FIG. 6. Alternatively, one or more straps 616 may extend around an upper corner of the chair. In such embodiments, one or more straps 616 can extend from one side of the head support 604, around the chair back 608, and to the top of the head support 604.

One embodiment of the invention was tested using a mannequin which was mechanically ventilated to produce air currents about the nose and mouth to simulate natural breathing. The head of the mannequin was placed on the head support of the air filtration device as a sleeping person might lie on a pillow on a bed. Prior to activating the device, the particle count in the region above the mannequin's mouth was approximately 12,000-16,000 particles of 0.5 microns or larger per 30 seconds with a sampling rate of 0.1 cubic feet per minute (CFM). The personal air filtration device was then activated with approximately 40 CFM of air blowing into a plenum within the head support at a pressure of approximately 0.125 inches of water and allowed to equilibrate for approximately 15 seconds. The particle count was measured again and was found to be approximately 15 particles per 30 seconds at the mannequin's mouth. This testing shows that the personal air filtration device is capable of creating an area of filtered air around the head of a sleeping person.

In the foregoing detailed description, the invention has been described with reference to specific embodiments. However, it may be appreciated that various modifications and changes can be made without departing from the scope of the invention.

What is claimed is:

1. A device for providing a zone of filtered air proximate a breathing zone of a user, the device comprising:
   a blower configured to provide an air flow;
   a filter in flow communication with the blower to filter the air flow;
   a head support in flow communication with the blower, the head support configured to be positioned underneath a head of the user, a majority of an upper surface of the head support being air permeable such that the air flow can be delivered through the air permeable portion uniformly across the majority of the upper surface to provide a laminar flow of filtered air to create the zone of filtered air proximate the breathing zone of the user, the head support having a pillow chamber.

2. The device of claim 1, wherein the support structures include one or more air flow passages.

3. The device of claim 1, further comprising: a hose having a distal end and a proximal end, the proximal end coupled to the blower and the distal end coupled to the head support.

4. The device of claim 3, wherein the filter is disposed within the distal end of the hose.

5. The device of claim 1, wherein the breathing zone comprises a volume of air available for inspiration of at least one (1) liter in proximity of a nose or a mouth of the user.

6. The device of claim 1, wherein the breathing zone is smaller than the zone of filtered air.

7. The device of claim 1, wherein the zone of filtered air has a particulate concentration less than 50% of an ambient particulate concentration.

8. The device of claim 1, wherein the filter is disposed within the blower.

9. The device of claim 1, wherein the filter is disposed downstream of the blower.

10. The device of claim 9, wherein the filter is a point of delivery filter, disposed within the head support and substantially coextensive with the air permeable portion.

11. The device of claim 10, wherein the air permeable portion includes a filter cover.

12. The device of claim 11, wherein the filter cover includes a hydrophobic composition or treatment.

13. The device of claim 9, wherein the air permeable portion is the filter.

14. The device of claim 1, wherein the filter is a HEPA filter.

15. The device of claim 1, wherein the filter is removable from the head support.

16. The device of claim 15, wherein the removable filter is secured to the head support by a mating zipper, wherein a first side of the mating zipper is attached to the filter and a second side of the mating zipper is attached to the head support.

17. The device of claim 1, wherein the blower is configured to provide an air flow having a flow rate of less than approximately one hundred (100) cubic feet per minute.

18. The device of claim 1, wherein the head support is adapted to be used on top of a pillow disposed in the pillow chamber.

19. The device of claim 18, wherein the pillow chamber is a pocket adapted to receive the pillow.

20. A device for creating a zone of filtered air proximate a head of a user, the device comprising:
   a blower configured to provide an air flow;
   a head support comprising an upper surface, wherein the upper surface comprises an air delivery surface in flow communication with the blower and in support of the head of the user, the air delivery surface comprising the majority of the upper surface of the head support configured to deliver air flow uniformly across the air delivery surface and to distribute the air flow as a laminar air flow to the zone of filtered air, the head support having a pillow chamber;
   an elongated hose providing flow communication between the blower and the air delivery surface;
   a filter disposed within the device for filtering the air flow before it is distributed to the zone of filtered air.

21. The device of claim 20, wherein the filter is disposed between the blower and the air delivery surface.

22. The device of claim 20, wherein the zone of filtered air comprises a volume of air available for inspiration of at least one (1) liter in proximity of a nose or a mouth of the user.

23. The device of claim 20, wherein the filter comprises the air delivery surface.

24. The device of claim 20, further comprising: a plenum in flow communication with the blower and adapted to collect and distribute the air flow to the air delivery surface at a pressure suitable for maintaining the zone of filtered air.

25. A method of creating a zone of filtered air proximate a breathing zone of a user, comprising:
  providing,
    i) a head support having an air permeable portion at an upper surface of the head support, the head support having a pillow chamber,
    ii) a blower in flow communication with the head support,
    iii) a plenum being adapted to distribute an air flow across the air permeable portion,
    iv) and a filter being disposed in flow communication with the blower;
  positioning the plenum in close proximity to the breathing zone of the user;
  actuating the blower, thereby providing the air flow to the plenum;
  directing the air flow through the filter; and
  directing the air flow to the plenum, thereby causing the plenum to inflate and direct the air flow across the majority of the air permeable portion to provide a laminar air flow of filtered air.

26. The method of claim 25, wherein the filter is disposed substantially coextensive with the air permeable portion of the plenum.

27. A method of providing a user with filtered air, the method comprising:
  providing a blower and a head support, the head support comprising an upper surface and a plenum disposed within the head support and in flow communication with the blower, the majority of the upper surface comprising an air delivery surface, the head support in support of the head of the user having a pillow chamber, the air delivery surface configured to deliver air uniformly across the majority of the upper surface, the plenum being adapted to distribute the air flow across the air delivery surface; and
  providing a laminar filtered air flow through the air delivery surface that surrounds a breathing zone of the user.

28. The method of claim 27, wherein the laminar filtered air flow is provided at a flow rate of less than 100 cubic feet per minute.

29. The method of claim 27, wherein the filtered air comprises air having a particulate concentration less than 50% of an ambient particulate concentration.

* * * * *